(12) United States Patent
Lugert et al.

(10) Patent No.: US 8,388,988 B2
(45) Date of Patent: *Mar. 5, 2013

(54) COSMETIC PREPARATION FOR COLORING OF EYELIDS AND EYEBROWS

(75) Inventors: Gerhard Lugert, Nürnberg (DE); Tatiana Appel, Oberasbach (DE)

(73) Assignee: Faber-Castell AG, Stein (DE)

( * ) Notice: Subject to any disclaimer, the term of this patent is extended or adjusted under 35 U.S.C. 154(b) by 1081 days.

This patent is subject to a terminal disclaimer.

(21) Appl. No.: 11/875,984

(22) Filed: Oct. 22, 2007

(65) Prior Publication Data

US 2008/0254075 A1    Oct. 16, 2008

(30) Foreign Application Priority Data

Oct. 20, 2006    (EP) ..................................... 06022005

(51) Int. Cl.
*A61K 8/72*    (2006.01)
*A61K 8/89*    (2006.01)
*A61Q 1/10*    (2006.01)

(52) U.S. Cl. .......................................... 424/401; 424/63
(58) Field of Classification Search .................... 424/401
See application file for complete search history.

(56) References Cited

U.S. PATENT DOCUMENTS

| 5,013,543 | A | | 5/1991 | Mercado et al. | |
|---|---|---|---|---|---|
| 5,776,241 | A | * | 7/1998 | Giacomoni et al. | 106/498 |
| 2002/0192170 | A1 | | 12/2002 | Appel et al. | |
| 2003/0082218 | A1 | * | 5/2003 | Ichinohe et al. | 424/401 |
| 2004/0191200 | A1 | * | 9/2004 | Lezer et al. | 424/70.11 |
| 2006/0093568 | A1 | * | 5/2006 | Blin et al. | 424/70.16 |

FOREIGN PATENT DOCUMENTS

| EP | 1247514 A2 | 10/2002 |
|---|---|---|
| JP | 2006-69965 A | 3/2006 |

* cited by examiner

*Primary Examiner* — Richard Schnizer
*Assistant Examiner* — Audrea Buckley
(74) *Attorney, Agent, or Firm* — Laurence A. Greenberg; Werner H. Stemer; Ralph E. Locher

(57) ABSTRACT

An aqueous cosmetic preparation for coloring of eyelids and eyebrows contains 3-35 wt. % of an aqueous plastic dispersion based on an acrylate polymer and having a 30-50% solids content, 1-20 wt. % of at least one alcohol being ethanol and/or propanol, 2-25 wt. % of at least one moisture-retention agent, 0.2-5 wt. % of a polyoxyethylene glycerin fatty acid ester and/or a polyether-modified polysiloxane, and a colorant. The preparation has a Brookfield viscosity at 25° C. of less than 50 mPa-sec.

9 Claims, No Drawings

COSMETIC PREPARATION FOR COLORING OF EYELIDS AND EYEBROWS

CROSS-REFERENCE TO RELATED APPLICATION

This application claims the priority, under 35 U.S.C. §119, of European application EP 06 022 005.0, filed Oct. 20, 2006; the prior application is herewith incorporated by reference in its entirety.

BACKGROUND OF THE INVENTION

Field of the Invention

The invention relates to a cosmetic preparation for coloring of eyelids and eyebrows. The coloring of these skin areas has been achieved heretofore principally with the use of relatively highly viscous preparations, applied with the aid of stiff brushes, paintbrushes, and the like. With these known measures, it was difficult to accurately apply the coloring. Further, the known measures require numerous withdrawals of preparation from a reservoir container, in order to achieve a uniform resulting application of the coloring material on the desired skin areas. In the course of the withdrawals, it is difficult to avoid dropping a certain amount of the cosmetic preparation from the application instrument. Accordingly, today this problem of handling of the material has been solved to some extent by the use (in typical cases) of capillary application instruments. However, with a capillary instrument the viscosity of the preparation must be kept relatively low in order to be able to conveniently remove the preparation from the reservoir. The combination of the requirements of low viscosity, high covering power, durability (time during which the coloring remains on the skin of the eyelid and/or eyebrow without fading or smearing), and easy removability with cold cream or other makeup remover, is difficult to satisfy. Low viscosity preparations tend to penetrate readily into the skin, rendering them more difficult to remove when desired. Also, they tend to accumulate in skin folds and skin pockets, and to "bleed" coloring material in and from these locations, making it difficult to produce colored regions which have uniform smooth edges. Instead, the appearance is irregular and sloppy.

A known aqueous preparation for eyelids and eyebrows, disclosed in published, Japanese patent application JP-A-2006-6995, contains, as a film-forming substance, a plastic dispersion based on acrylate copolymer(s), with a solids content of the copolymers of 2-20 weight percent (wt. %) of the total weight of the preparation, and is further formed of: a pigment (1-40 wt. %), a moisture-retention agent such as ethylene glycol or glycerin (3-20 wt. %); and a polyether-modified polysiloxane (0.05-5 wt. %).

BRIEF SUMMARY OF THE INVENTION

It is accordingly an object of the invention to provide a cosmetic preparation for coloring of eyelids and eyebrows which overcomes the above-mentioned disadvantages of the prior art compositions of this general type, and to devise an alternative cosmetic preparation for coloring of eyelids and eyebrows.

The problem is solved by an aqueous preparation containing an aqueous plastic dispersion (30-50 wt. % solids) based on acrylate polymer(s) (3-35 wt. %), at least one alcohol from the group of ethanol and propanol (1-20 wt. %); at least one moisture-retention agent (2-15 wt. %); a polyoxyethylene glycerin fatty acid ester and/or a polyether-modified polysiloxane (0.2-5 wt. %); and a colorant, which may contain a mixture of colorants. The preparation has a Brookfield viscosity (25° C.) of less than 50 mPa-sec.

Such a preparation can be easily applied with a capillary instrument to eyelids and eyebrows, without problems. The preparation does not "bleed" into skin folds and skin pockets. This non-bleeding property is attributable to the acrylate copolymer particles and the alcohols (ethanol and/or propanol). The preparation dries readily on the skin, which reduces the risk of smudging during application, and contributes to reduction of the tendency of the liquid to flow into skin folds. The alcohols (ethanol, propanol) also have a certain embrittling and stiffening effect as a result of their tendency to withdraw moisture and fats from the skin; however, according to the invention this effect is compensated for by the presence of moisture-retention agent(s) along with the alcohol(s). Preferred moisture-retention agents are 1,3-butanediol, propylene glycol, and glycerin. If glycerin is used, preferably it is used in combination with one of the other two named moisture-retention agents. The combination of moisture-retention agent(s) and alcohol(s) also favors storability of an applicator filled with the preparation. In preparations of the described type, which are somewhat volatile, there is a risk that during storage (e.g. a period of non-use) an applicator will suffer clogging of its (the applicator instrument's) pores and/or capillary channel(s) by drying of material which has been drawn into it/them, whereby the functionality of the applicator becomes limited or (possibly) the applicator becomes unusable. It has been found that this undesirable effect is at least retarded, to enable longer storage times, by the presence of a combination of at least one alcohol from the group of ethanol and propanol and at least one moisture-retention agent.

In order to provide sufficiently low viscosity for use in a capillary applicator, despite the presence of viscosity-increasing substances in the preparation, particularly the above-mentioned plastic particles and (e.g.) also the pigments added as colorants, there is/are added the polyoxyethylene glycerin fatty acid ester, the polyether-modified polysiloxane, or preferably a mixture of these. One property of these materials is that they counteract the increase in viscosity brought about (e.g.) by the plastic dispersion. In this connection, it was surprising that the preparation, particularly a preparation containing both of the substances, nonetheless had a low tendency to flow into skin folds. When the content of such substance (or mixture) is greater than 5 wt. %, this prevention is no longer assured. When the content is below 0.5 wt. %, there is no substantial viscosity-reducing effect.

Depending on the degree of coloration desired, the proportion of colorants is in the range 0.5-30 wt. %. Preferably the colorants are pigments, which usually provide a stronger coloring than soluble colorants (dyes and the like). It is possible to use the preparation in a capillary system without problems if the particle size distribution of the pigment(s) is characterized by D90%<10 micron. The moisture or water content of the preparation is in the range 30-70 wt. %.

The total content of additives, e.g. skin care agents such as aloe vera, *Camilla sinensis*, tocopherol, or panthenol, and e.g. preservatives, is preferably limited to 5 wt. %.

Other features which are considered as characteristic for the invention are set forth in the appended claims.

Although the invention is described herein as embodied in a cosmetic preparation for coloring of eyelids and eyebrows, it is nevertheless not intended to be limited to the details described, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

DETAILED DESCRIPTION OF THE INVENTION

Example 1

| A black eyeliner liquid with Brookfield viscosity approximately 11 mPa-sec (20° C.): | |
|---|---|
| water, demineralized | 27.0 wt. % |
| polyethylene glycerin stearic acid ester (CAS 68553-11-7): | 2.0 wt. % |
| polyether modified polysiloxane ("ABIL B 8851", provided by Degussa, Germany): | 1.0 wt. % |
| D&C Black #2 ("Covarine W 9793", provided by Sensient Cosmetic Technologies/LCW, F-95310 Saint Ouen L'Aumone, France): | 20.0 wt. % |
| glycerin | 4.0 wt. % |
| propylene glycol | 8.0 wt. % |
| ethanol | 8.0 wt. % |
| plastic dispersion based on acrylate copolymer(s) ("Syntran PC 5112", provided by Interpolymer S.a.r.l., F-67162 Wissembourg, France), with total solids 35 wt. %: | 20.0 wt. % |

Example 2

| A blue-gray eyeliner liquid with Brookfield viscosity approximately 8 mPa-sec (25° C.): | |
|---|---|
| water | 61.0 wt. % |
| propylene glycol | 12.0 wt. % |
| ethanol | 5.0 wt. % |
| polyethylene glycerin stearic acid ester (CAS 68553-11-7): | 1.0 wt. % |
| phenoxyethanol (preservative) | 0.5 wt. % |
| D&C Black #2 ("Covarine W 9793", provided by Sensient Cosmetic Technologies/LCW, F-95310 Saint Ouen L'Aumone, France): | 10.0 wt. % |
| Brilliant Blue FCF dye (C.I. 42090) | 0.5 wt. % |
| dispersion of a styrene/acrylate/ammonium methcarylate copolymer ("Syntran 5760", provided by Interpolymer S.a.r.l., F-67162 Wissembourg, France), with total solids 41 wt. %: | 10.0 wt. % |

Example 3

| A reddish-brown eyeliner liquid with Brookfield viscosity approximately 15 mPa-sec (25° C.): | |
|---|---|
| water | 53.28 wt. % |
| 1,3-butanediol | 12.0 wt. % |
| propanol | 3.0 wt. % |
| phenoxyethanol | 0.5 wt. % |
| polyether modified polysiloxane ("ABIL B 8843", provided by Degussa, Germany): | 3.0 wt. % |

-continued

| A reddish-brown eyeliner liquid with Brookfield viscosity approximately 15 mPa-sec (25° C.): | |
|---|---|
| plastic dispersion based on acrylate copolymer(s) ("Syntran PC 5112", provided by Interpolymer S.a.r.l., F-67162 Wissembourg, France), with total solids 35 wt. %: | 25.0 wt. % |
| FD&C Red No. 40 dye (C.I. 16035) | 3.0 wt. % |
| Brilliant Blue FCF dye (C.I. 42090) | 0.22 wt. % |

The invention claimed is:

1. An aqueous cosmetic preparation for coloring of eyelids and eyebrows, consisting of:
   3-35 wt. % of an aqueous plastic dispersion based on an acrylate polymer and having solids content of 30-50 wt. %;
   1-20 wt. % of alcohol, wherein the alcohol is ethanol, propanol, or a mixture of ethanol and propanol;
   2-15 wt. % of a moisture-retention agent, wherein the moisture-retention agent is selected from the group consisting of a single moisture-retention agent and a plurality of moisture-retention agents;
   0.2-5 wt. % of a polyoxyethylene glycerin fatty acid ester;
   a colorant;
   a content of water being 30-70 wt. %; and
   a content of additives being less than or equal to 5 wt. %, the additives selected from the group consisting of skincare agents and preservatives;
   the preparation has a Brookfield viscosity at 25° C. of less than 50 mPa-sec.

2. The preparation according to claim 1, wherein a content of said colorant is 0.5-30 wt. %.

3. The preparation according to claim 2, wherein said colorant has at least one pigment with a particle size distribution characterized by D90%<10 micron.

4. An aqueous cosmetic preparation for coloring of eyelids and eyebrows, consisting of:
   3-35 wt. % of an aqueous plastic dispersion based on an acrylate polymer and having solids content of 30-50 wt. %;
   1-20 wt. % of alcohol, wherein the alcohol is ethanol, propanol, or a mixture of ethanol and propanol;
   2-15 wt. % of a moisture-retention agent, wherein the moisture-retention agent is selected from the group consisting of a single moisture-retention agent and a plurality of moisture-retention agents;
   0.2-5 wt. % of a mixture of a polyoxyethylene glycerin fatty acid ester and a polyether-modified polysiloxane;
   a colorant;
   a content of water being 30-70 wt. %; and
   a content of additives being less than or equal to 5 wt. %, the additives selected from the group consisting of skincare agents and preservatives;
   the preparation has a Brookfield viscosity at 25° C. of less than 50 mPa-sec.

5. The preparation according to claim 4, wherein a content of said colorant is 0.5-30 wt. %.

6. The preparation according to claim 5, wherein said colorant has at least one pigment with a particle size distribution characterized by D90%<10 micron.

7. An aqueous cosmetic preparation for coloring of eyelids and eyebrows, consisting of:

3-35 wt. % of an aqueous plastic dispersion based on an acrylate polymer and having solids content of 30-50 wt. %;

1-20 wt. % of alcohol, wherein the alcohol is ethanol, propanol, or a mixture of ethanol and propanol;

2-15 wt. % of a moisture-retention agent, wherein the moisture-retention agent is selected from the group consisting of a single moisture-retention agent and a plurality of moisture-retention agents;

0.2-5 wt. % of a polyether-modified polysiloxane;

a colorant;

a content of water being 30-70 wt. %; and a content of additives being less than or equal to 5 wt. %, the additives selected from the group consisting of skin-care agents and preservatives;

the preparation has a Brookfield viscosity at 25° C. of less than 50 mPa-sec.

8. The preparation according to claim 7, wherein a content of said colorant is 0.5-30 wt. %.

9. The preparation according to claim 8, wherein said colorant has at least one pigment with a particle size distribution characterized by D90%<10 micron.

* * * * *